United States Patent
Mihara (10) Patent No.: US 7,592,167 B2
(45) Date of Patent: Sep. 22, 2009

(54) FUNCTIONAL PEPTIDE FIBER, PRODUCTION THEREOF AND METHOD FOR RECOVERING PEPTIDE CHAINS

(75) Inventor: Hisakazu Mihara, Chigasaki (JP)

(73) Assignee: Fuji Xerox Co., Ltd., Tokyo (JP)

( * ) Notice: Subject to any disclaimer, the term of this patent is extended or adjusted under 35 U.S.C. 154(b) by 6 days.

(21) Appl. No.: 11/896,711

(22) Filed: Sep. 5, 2007

(65) Prior Publication Data

US 2008/0199934 A1     Aug. 21, 2008

Related U.S. Application Data

(62) Division of application No. 10/241,631, filed on Sep. 12, 2002, now abandoned.

(30) Foreign Application Priority Data

Feb. 26, 2002    (JP)   ............... 2002-049977

(51) Int. Cl.
    *C07K 2/00*     (2006.01)
    *C07K 16/00*     (2006.01)
    *C12N 9/16*     (2006.01)

(52) U.S. Cl. .................... 435/188; 530/300; 530/391.1; 530/344

(58) Field of Classification Search ...................... 514/8, 514/12; 530/350, 391.1, 300, 344; 435/7.5, 435/188; 428/300.1
See application file for complete search history.

(56) References Cited

OTHER PUBLICATIONS

Takahashi, Y. et al., "Construction of Peptides that Undergo Structural Transition from α-Helix to β-Sheet and Amyloid Fibril Formation by the Introduction of N-Terminal Hydrophobic Amino Acids," *Tetrhedron* 56: 7011-7018 (2000).
Takahashi, Y. et al., "Heterogeneous Assembly of Complementary Peptide Pairs into Amyloid Fibrils with α- β Structural Transition," *Chembiochem* 1: 75-79 (2001).
Takahashi, Y. et al., "Optimization of Hydrophobic Domains in Peptides That Undergo Transformation from α-Helix to β-Fibril," *Bioorganic & Medicinal Chemistry* 7: 177-185 (1999).
Takahashi, Y. et al., "Mutational analysis of designed peptides that undergo structural transition from α helix to β sheet and amyloid fibril formation," *Structure* 8(9): 915-925 (2000).
Heslot, Biochimie 80, 19-31, (1998).
Takahashi, Y. et al., "Design of a Peptide Undergoing α-β Structural Transition and Amyloid Fibrillogenesis by the Introduction of a Hydrophobic Defect," Chem. Eur. J. 1998, 4, No. 12, pp. 2475-2484.
Reprint of Lecture of Biofunction-related Chemical Symposium, 2000, 15th, p. 314-315.
Function & Materials, 2001, Oct. 21, p. 11-17.

*Primary Examiner*—Chih-Min Kam
(74) *Attorney, Agent, or Firm*—Oliff & Berridge, PLC (57) ABSTRACT

This invention provides a functional peptide fiber which comprises a plurality of peptide structure units each containing at least one peptide chain, wherein peptide chains contained in each adjacent peptide structure units do not form peptide bond but are structured into a fibrous form by taking a β-sheet structure, and wherein at least one of the plurality of peptide structure units contains a peptide chain having a functional material connected thereto. Also disclosed are a method for producing the functional peptide fiber and a method for recovering peptide chains from the functional peptide fiber.

13 Claims, 3 Drawing Sheets

FUNCTIONAL PEPTIDE FIBER, PRODUCTION THEREOF AND METHOD FOR RECOVERING PEPTIDE CHAINS

This application is a divisional of U.S. application Ser. No. 10/241,631, filed Sep. 12, 2002, now abandoned. The entire disclosure of the prior application is hereby incorporated by reference herein in its entirety.

FIELD OF THE INVENTION

This invention relates to a method for producing a functional peptide fiber having a desired function and to a method for recovering peptide chains.

DESCRIPTION OF THE RELATED ART

α-Helix structure and β-sheet structure are known as possible secondary structures of peptide chain in which a large number of amino acid residues are peptide-bonded. The three-dimensional structure of various proteins is composed mainly of these α-helix structure and β-sheet structure. One strand of amino acid sequence constituting a protein has a structure in which α-helix and β-sheet are intricately connected, and a large number of studies have been reported on the relationship between these amino acid sequences and tertiary structures.

Three-dimensional structure of protein is roughly classified into (1) spherical and (2) fibrous. Proteins such as enzymes and antibodies take a spherical structure, and the fibrous structure can be found in muscle fiber and silk. The β-sheet structure is a stable structure which is obtained when β-strands (β-structures) are arranged in a row in parallel or anti-parallel due to generation of hydrogen bond and electrostatic and hydrophobic interactions between β-strands. Although spherical proteins contain α-helix structure and β-sheet structure owing to local β-strands, this structure is different from that mentioned above. In a peptide fiber such as silk, hundreds of (or a large number of) peptide β-strands are strictly organized regularly in a row and made into a stable fibrous form.

Peptide fibers can be regarded as excellent materials from the environmental point of view, because they are stable and broadly distributed in the natural world as an element of protein and have naturally degrading property. Accordingly, in case that a certain function can be added to a functional peptide fiber based on a fibrous structure, it could be used in a broad range of applications and also as a material suited for recycling.

However, each of the peptide fibers existing in the natural world is generally constituted by folding of one peptide chain at every length of β-strand, and nothing is known about a method effective in incorporating functionality in the fibers.

The present inventors found a method for artificially producing a characteristic β-sheet structure (Takahashi, Y., Ueno, A. and Mihara, H., *Chem. Eur. J.*, 4, pp. 2475-2484 (1998)). In this method, a β-peptide structure is obtained by introducing a hydrophobic group such as adamantane carbonyl group or octanoyl group into the amino terminal of a peptide chain of an amino acid sequence constituting a parallel double-stranded α-helix structure, mixing the product in an aqueous solution, and effecting rearrangement of the α-helix structure into β-sheet structure spontaneously and self-catalytically under a uniform environment. That is, although peptides are not connected covalently in the peptide fiber obtained by this method, but two or more peptide chains are constructed into a stable form due to their arrangement in a row through hydrogen bonds.

In case that functional materials can be connected making use of the β-sheet constituted by a large number of the peptide chains, not only functional peptide fibers having various functionality can be provided, but also a large number of peptide chains can be used as effective materials which can be easily recovered and recycled by cutting their assembly using an organic solvent or an acid or alkali solution.

SUMMARY OF THE INVENTION

Accordingly, an object of the invention is to provide a structure (functional peptide fiber) produced by adding functionality to a peptide fiber Another object of the invention is to provide an effective method for producing the functional peptide fiber.

A still other object of the invention is to provide a method for recovering peptide chains from the functional peptide fiber.

Other objects and effects of the present invention will become apparent from the following description.

Taking such actual circumstances into consideration, the present inventors have conducted extensive studies and, as a result of the efforts, accomplished the invention by finding a function-added peptide fiber structure and its effective production method and a method for recovering peptide chains from the functional peptide fiber.

That is, the above-described objects of the invention have been achieved by providing the followings.

(1) A functional peptide fiber which comprises a plurality of peptide structure units each containing at least one peptide chain, wherein peptide chains contained in each adjacent peptide structure units do not form peptide bond but are structured into a fibrous form by taking a β-sheet structure, and wherein at least one of said plurality of peptide structure units contains a peptide chain having a functional material connected thereto.

(2) The functional peptide fiber according to item (1) above, wherein the functional material is connected to the amino terminal or carboxyl terminal of the peptide chain.

(3) The functional peptide fiber according to item (1) above, wherein the functional material is connected to the peptide chain via a connecting substance which specifically connects to the peptide chain and the functional material.

(4) The functional peptide fiber according to item (3) above, wherein the connecting substance is connected to the amino terminal or carboxyl terminal of the peptide chain.

(5) The functional peptide fiber according to item (3) or (4) above, wherein the connecting substance is a material which connects to the functional material with a biochemical specificity.

(6) The functional peptide fiber according to item (3) above, wherein the connecting substance is a pair of materials that connect to each other with a biochemical specificity, and one member of said pair of materials is connected to the peptide chain side, and the other member to the functional material side.

(7) The functional peptide fiber according to item (6) above, wherein said one member to be connected to the peptide chain side is connected to the amino terminal or carboxyl terminal of the peptide chain.

(8) The functional peptide fiber according to item (6) or (7) above, wherein said pair of materials comprise any one pair of: biotin group and avidin group; an antibody and its antigen; and an enzyme and its substrate, inhibitor or coenzyme.

(9) The functional peptide fiber according to item (3) above, wherein the connecting substance comprises a pair of a metal and a ligand of the metal, and either one of the metal and the ligand is connected to the peptide chain side, and the other to the functional material side.

(10) The functional peptide fiber according to any one of items (1) to (9) above, wherein the functional material comprises at least one material selected from the group consisting of proteins, carbohydrates, lipids, coenzymes, pigments containing fluorescence groups, liquid crystalline molecules and metallic ligands.

(11) The functional peptide fiber according to any one of items (1) to (10) above, wherein the peptide structure unit itself contains one peptide chain structured into a β-sheet form.

(12) The functional peptide fiber according to any one of items (1) to (11) above, wherein a peptide structure unit adjacent to the peptide structure unit having a functional material connected thereto contains a peptide chain having connected thereto a group different from the functional material.

(13) The functional peptide fiber according to item (12) above, wherein the different group is carboxyl group or amino group.

(14) The functional peptide fiber according to item (12) above, wherein the different group is a second functional material different from said functional material.

(15) The functional peptide fiber according to item (1) above, wherein at least two of said plurality of peptide structure units have a functional material connected thereto.

(16) The functional peptide fiber according to item (15) above, which comprises, between said at least two peptide structure units each having a functional material, a peptide structure unit forming a β-sheet structure with peptide chains of said functional material-having peptide structure units and containing a peptide chain having connected thereto a group different from the functional material.

(17) The functional peptide fiber according to any one of items (1) to (16) above, wherein said plurality of peptide structure units contains a peptide chain comprising a plurality of peptide chains in which adjacent terminals thereof are bonded to each other.

(18) The functional peptide fiber according to item (17) above, wherein the terminals of said plurality of peptide chains are disulfide-bonded.

(19) The functional peptide fiber according to any one of items (1) to (18) above, wherein the β-strand moiety constituting the β-sheet structure has a number of amino acid residues of from 5 to 30.

(20) The functional peptide fiber according to any one of items (1) to (19) above, wherein the number of amino acid residues constituting a peptide chain contained in the peptide structure unit is 200 or less.

(21) A method for producing a functional peptide fiber, which comprises mixing a plurality of peptide structure units in an aqueous solution to thereby make the plural peptide structure into a β-sheet structure to have a fibrous form, wherein said plurality of peptide structure units each contains at least one peptide chain, and wherein at least one of said plurality of peptide structure units contains a peptide chain having connected thereto a functional material, a connecting substance to be connected to a functional material, or the functional material via the connecting substance.

(22) The method for producing a functional peptide fiber according to item (21) above, wherein at least two of said plurality of peptide structure unit contain a peptide chain having the functional material or the connecting substance.

(23) The method for producing a functional peptide fiber according to item (21) or (22) above, wherein said plurality of peptide structure units include a peptide structure unit having connected thereto a material different from the functional material or the connecting substance.

(24) The method for producing a functional peptide fiber according to item (21) above, wherein the connecting substance is a substance that connects to the functional material with a biochemical specificity.

(25) The method for producing a functional peptide fiber according to item (21), (22) or (23) above, wherein the connecting substance is one member of a pair of materials that connect to each other with a biochemical specificity.

(26) The method for producing a functional peptide fiber according to item (25) above, wherein said pair of materials comprise any one pair of: biotin group and avidin group; an antibody and its antigen; and an enzyme and its substrate, inhibitor or coenzyme.

(27) The method for producing a functional peptide fiber according to item (21) above, wherein the connecting substance is a pair of a metal and a ligand of the metal, and either one of the metal and the ligand is connected to the peptide chain side, and the other to the functional material side.

(28) The method for producing a functional peptide fiber according to any one of items (21) to (27) above, wherein the functional material comprises at least one material selected from the group consisting of proteins, carbohydrates, lipids, coenzymes, pigments containing fluorescence groups, liquid crystalline molecules and metallic ligands.

(29) The method for producing a functional peptide fiber according to any one of items (21) to (28) above, wherein the functional material or the connecting substance is connected to the amino terminal or carboxyl terminal of the peptide chain.

(30) The method for producing a functional peptide fiber according to item (23) above, wherein the number of β-strands contained in the peptide structure unit containing a peptide chain having the functional material or the connecting substance and that in the peptide structure unit containing a peptide chain having the different material, mixed in the aqueous solution, is different.

(31) The method for producing a functional peptide fiber according to any one of items (21) to (30) above, further comprising connecting the functional material to the connecting substance after the formation of the β-sheet structure.

(32) The method for producing a functional peptide fiber according to item (25), (26) or (27) above, further comprising, after the formation of the β-sheet structure, connecting a functional material containing the other member of said pair of materials to said one member connected to the β-sheet structure with a biochemical specificity.

(33) The method for producing a functional peptide fiber according to any one of items (21) to (32) above, wherein said plurality of peptide structure units comprising a peptide chain having a hydrophobic group at a terminal thereof.

(34) The method for producing a functional peptide fiber according to any one of items (21) to (33) above, wherein the peptide chains contained in said plurality of peptide structure units have α-helix structure before structured into β-sheet form.

(35) The method for producing a functional peptide fiber according to any one of items (21) to (34) above, wherein said plurality of peptide structure units contains a peptide chain comprising a plurality of peptide chains in which adjacent terminals thereof are bonded to each other.

(36) The method for producing a functional peptide fiber according to item (35) above, wherein the terminals of said plurality of peptide chains are disulfide-bonded.

(37) The method for producing a functional peptide fiber according to any one of items (21) to (36) above, wherein said plurality of peptide structure units contain peptide chains that are constructed into β-sheet form before making β-sheet form with peptide chains contained in other peptide structure units.

(38) The method for producing a functional peptide fiber according to any one of items (21) to (37) above, wherein β-strand moieties constituting the β-sheet structure each has a number of amino acid residues from 5 to 30.

(39) The method for producing a functional peptide fiber according to any one of items (21) to (38) above, wherein peptide chains contained in the respective peptide structure unit have a number of amino acid residues of 200 or less.

(40) A method for recovering peptide chains, which comprises:

mixing a functional peptide fiber according to any one of items (1) to (20) above in an organic solvent or an acid or alkali solution to divide it into a plurality of peptide chains; and recovering said plurality of peptide chains from the solvent or solution.

The term "peptide structure unit" as used herein means a partial structure containing a peptide chain which forms β-sheet structure together with other peptide chain. For example, a single peptide chain alone or two or more of them, peptide chains already structured into β-sheet form, two or more peptide chains in which terminals of the two or more chains are bonded, and combinations thereof can be cited. These peptide chains form the β-sheet structure together with other peptide chains.

According to the functional peptide fiber of the invention, it is desirable that a functional material which exerts a desired function is connected via a connecting substance capable of specifically connecting to the peptide chain and the functional material.

By constituting in this manner, the choices of functional materials that can be connected to peptide chains can be expanded.

It is desirable that the connecting substance to be used herein is a material which connects to the terminal of the peptide chain and the functional material mutually having biochemical specificity when they are connected, and it may be a material which connects to the functional material itself with a biochemical specificity or a material that connects one of a pair of materials to the peptide chain side, and the other to the functional material side.

It is particularly desirable to connect the functional material to a connecting substance which connects the functional material to the peptide chain terminal biochemically specifically. This is because the peptide chain terminal can be chemically modified easily in comparison with other parts of the peptide chain, and the connecting position of the functional material in the functional peptide fiber can be easily controlled by connecting a biochemically specific connecting substance to this terminal.

In this connection, when used as a fibrous peptide structure, it is desirable that the peptide fiber is composed of 100 or more of β-strands. Also, it is desirable that the number of amino acid residues of the β-strand which constitutes the β-sheet structure is from 5 to 30.

BRIEF DESCRIPTION OF THE DRAWINGS

In the drawings, 10 denotes a functional peptide fiber, 11, 12 and 13 denote peptide structure units, 211, 212, 221 and 222 denote connecting substances, and 2, 213 and 223 denote functional materials.

DETAILED DESCRIPTION OF THE INVENTION

The following describes the invention further in detail with reference to embodiments of the functional peptide fiber of the invention, but the invention is not restricted thereby.

First Embodiment

Figure 1:
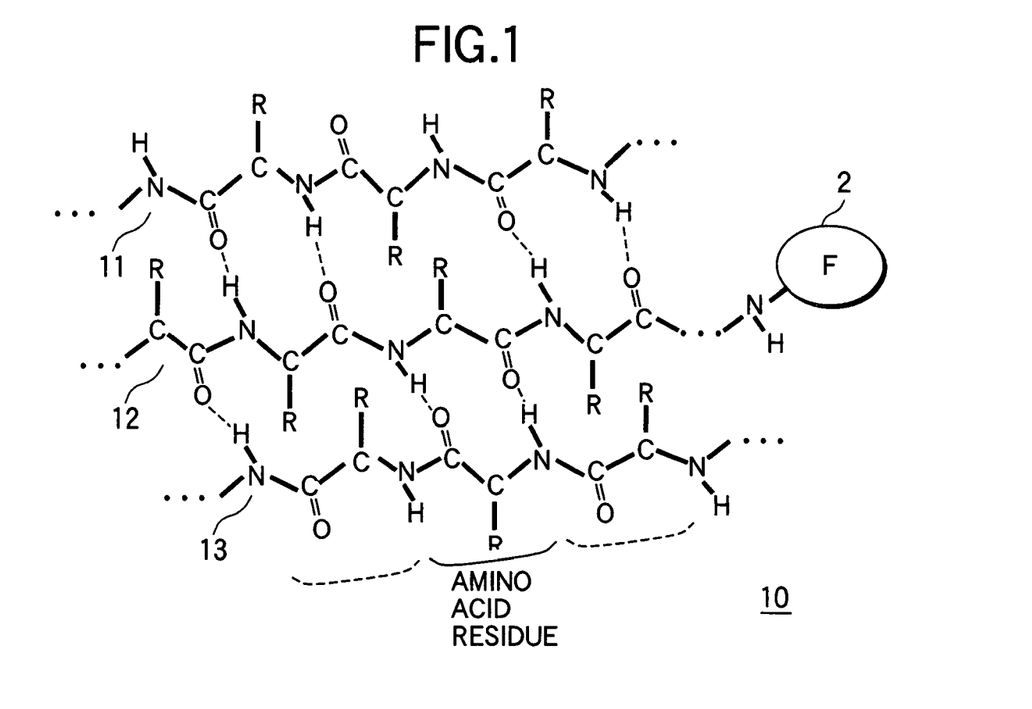
FIG. 1 is a schematic illustration showing the functional peptide fiber of the first embodiment of the invention.

The first embodiment of the functional peptide fiber of the invention is shown in FIG. 1.

The functional peptide fiber 10 of the invention is a fibrous structure comprised of two or more peptide chains (β-strands), but three peptide chains 11, 12 and 13 are picked out and illustrated in the drawing. These three β-strands are adjoined in parallel or antiparallel and mutually bonded to a direction orthogonal to the longitudinal direction of the peptide chains through their hydrogen bonds (shown by broken lines). In this embodiment, each of these three peptide chains corresponds to the peptide structure unit of the invention, and, particularly, the peptide chain 12 to which a functional material 2 is connected corresponds to a first peptide structure unit. As is well known, a side chain R corresponding to each amino acid is connected to the asymmetric carbon of each amino acid residue. Structural stability of the β-sheet structure is obtained by the hydrogen bonds between these peptide chains. On the other hand, this functional peptide fiber is excellent in the recycling ability, because it is easily degraded into two or more peptide chains by mixing it with an organic solvent such as methanol.

Examples of the functional material to be connected to this peptide fiber include a protein, carbohydrate, lipid or coenzyme having a desired function, as well as a pigment containing a fluorescence group, a liquid crystalline molecule which forms orientation under electric field or by its heating and cooling and a metallic ligand having the ability to connect to the metal.

The peptide fiber of such a constitution is structurally stable and has the functionality excellent for the environment.

There are various sequences of amino acids taking the β-sheet structure, and they can be synthesized by a method such as the Fmoc method or can be used by cutting out from a natural protein, but they can be constructed based, e.g., on the studies already reported by the present inventors (Takahashi, Y., Ueno, A. and Mihara, H., *ChemBioChem*, 2, pp. 75-79 (2001); Takahashi, Y., Ueno, A. and Mihara, H., *Bioorg. Med. Chem.*, 7, pp. 177-185 (1999); Takahashi, Y., Ueno, A. and Mihara, H., *Structure*, 8, pp. 915-925 (2000);

Takahashi, Y., Yamashita, T., Ueno, A. and Mihara, H., *Tetrahedron*, 56, pp. 7011-7018 (2000)).

Though a functional material was bonded to an amino terminal in the first embodiment, it is possible to connect it to a carboxyl terminal, or the functional material can be connected to both terminals. Alternatively, it is possible to connect it to an amino acid residue side chain of the peptide chain. In this case, the functional material can be connected to the peptide chain directly or via a connecting substance. It is possible also to connect the functional material to the peptide chain terminals in two or more or all of the peptide structure units.

In this connection, it has been found from a result of tests that construction of one β-strand constituting the functional peptide fiber into a chain of from 5 to 30 amino acid residues is most suited for making the β-sheet structure, and such a case is also desirable from the view point of the recovery of peptide chains at the time of the degradation of the structure.

Second Embodiment

Figure 2:
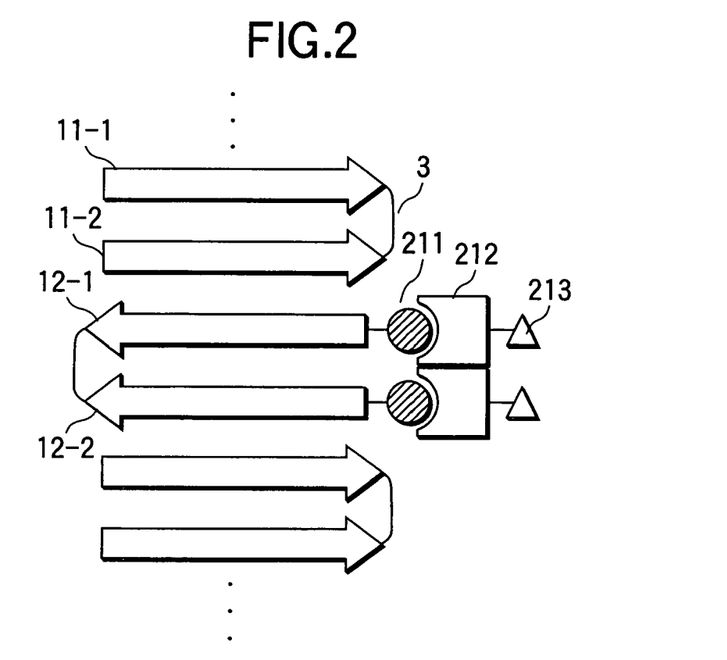
FIG. 2 is a schematic illustration showing the functional peptide fiber of the second embodiment of the invention.

In this embodiment, peptide chains having β-sheet structure were used as peptide structure units which constitute the functional peptide fiber (FIG. 2).

In FIG. 2, each of the open arrows indicates one peptide β-strand, and its direction is a direction from the amino group toward carboxyl group of the amino acid residues. Though the β-sheet structure was formed by mutually reversed direction of peptide chains (anti-parallel β-sheet) in the first embodiment, it is known that it is possible to form the β-sheet structure even in the same direction (parallel β-sheet).

Regarding the peptide structure units of this embodiment, a functional peptide fiber is formed by using a parallel β-sheet composed of two β-strands 11-1 and 11-2 of the same direction as one unit, and further arranging in the reverse direction a β-sheet structure connected with a functional material on both terminals as a peptide structure unit (12-1, 12-2). In this connection, either an anti-parallel β-sheet or a β-helix structure in which peptide chains having β-sheet structure are lined in a spiral form can be used as the peptide structure unit.

In this case, one connecting group 211 of a pair of connecting substances which mutually connect specifically is connected in advance to the peptide terminal to form the β-sheet structure, and then a functional material 213 which exerts a desired function is bonded specifically to this connecting group via the other connecting group 212 connected to the functional material 213 side. The β-sheet structure is a stable structure which is spontaneously formed by peptide chains in an aqueous solution, and there is a case in which the β-sheet structure cannot be formed easily when functional materials are connected in advance to peptide chains due, e.g., to the three-dimensional structure and polarization condition possessed by these functional materials, but this embodiment renders possible reduction of such a limitation during the β-sheet structure forming process. Examples of such a pair of connecting substances include avidin and biotin, an antibody and its antigen, an enzyme and its substrate, inhibitor or coenzyme and a metal and its ligand.

It is possible to connect a functional material directly to the β-peptide fiber, and it can also be connected via a single connecting substance. However, it becomes possible to connect a functional material selectively to the peptide terminal by the use of a connecting substance which connects having a biochemical specificity.

Also, cysteine (Cys) residues on the carboxyl terminals of two peptide chains which become a peptide structure unit are bonded by intermolecular disulfide bond 3. When paralleled two or more peptide chains whose terminals are bonded in this manner are used as one peptide structure unit, the β-sheet structure is easily formed between these two peptide chains, and intervals of functional materials can be easily changed by the adjoining of such a peptide structure unit containing two or more peptide chains. In this connection, it is possible to connect the peptide chain terminals by the connection or cross-linking of alkyl chains in addition to the disulfide bond. However, in case that two or more peptide chains are formed, disulfide bond is desirable from the viewpoint that their terminals can be connected relatively easily by preparing two or more peptide chains in advance.

Figure 3:
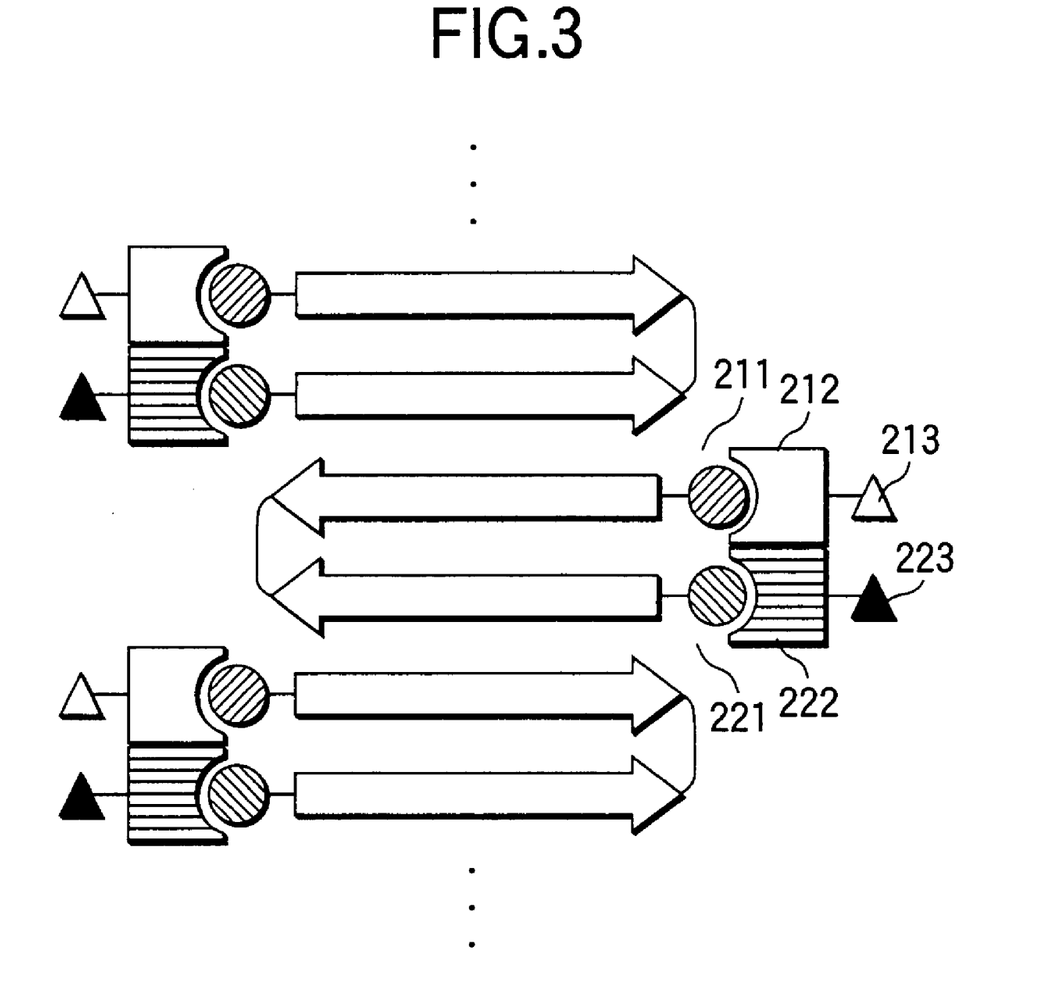
FIG. 3 is a schematic illustration showing a modified example of the functional peptide fiber of the second embodiment of the invention.

In case that functional peptide fibers comprised of more large number of peptide chains are formed, it becomes possible to change connecting positions of functional materials in these peptide fibers. Examples of the method for controlling arranging intervals of functional materials include, a method in which the mixing number of β-strands contained in the first and second structure units are varied and functional materials are arranged by dispersing them at intervals in response to the ratio and a method in which the number of β-strands in the first or second peptide structure unit is varied. Also, when a peptide structure unit has two terminals, it is possible to connect different functional materials 213 and 223 to respective terminals (FIG. 3). In this case, each of the functional materials 213 and 223 is connected to the peptide chain terminal via a connecting group which performs specific connecting, and the use of different connecting groups 211 and 221 to be connected to the peptide chain terminal side renders possible the use of different connecting groups 212 and 222 which can be specifically connected to the former connecting groups respectively and the use of different functional materials 213 and 223 to be connected thereto. It is possible also to connect a functional material only to a connecting group of one terminal of the peptide chain.

Since functional materials are connected to a β-sheet structure having periodicity in the functional peptide fiber obtained in this manner, the functional materials can be made into an aligned state.

Third Embodiment

Figure 4:
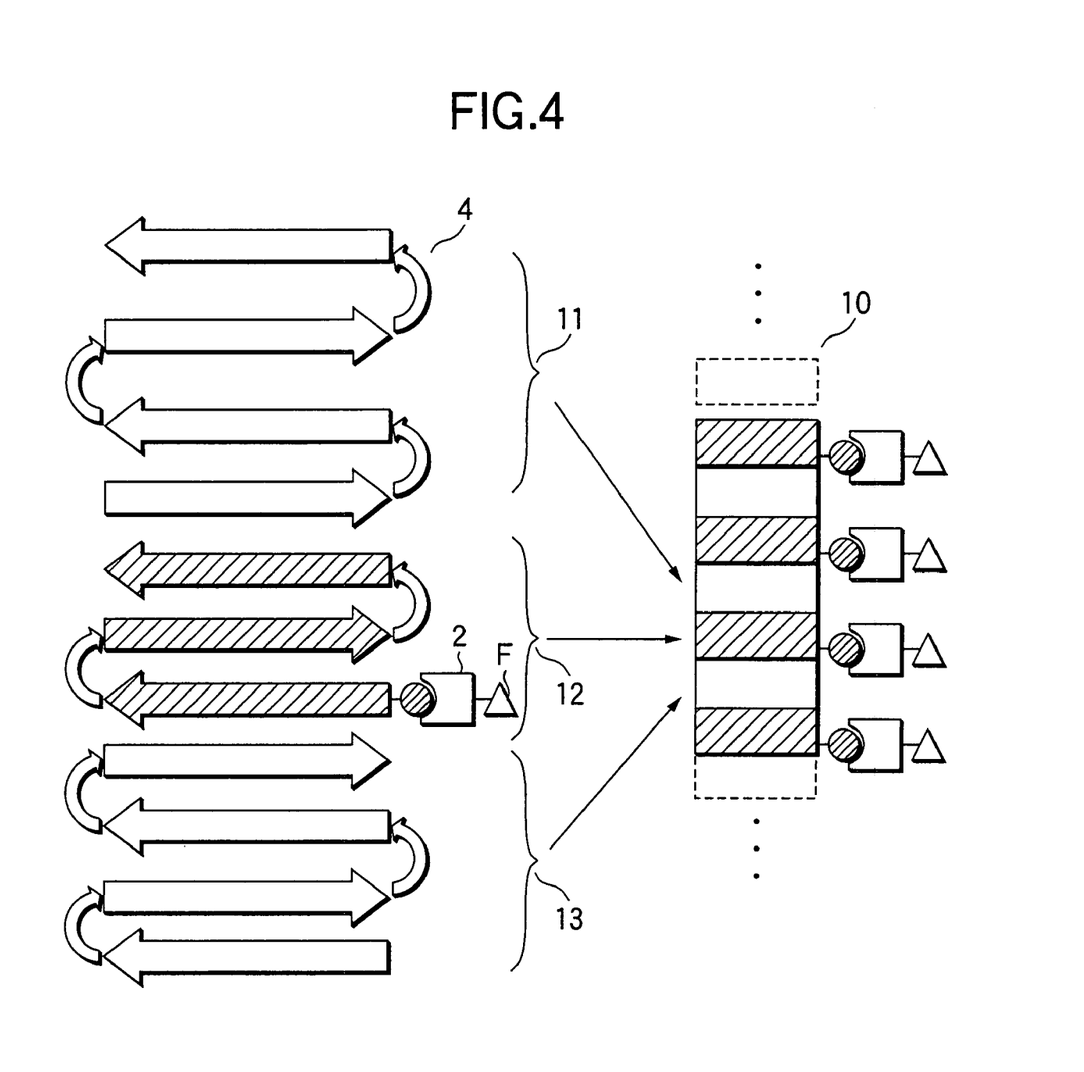
FIG. 4 is a schematic illustration showing the functional peptide fiber of the third embodiment of the invention.

As shown in FIG. 4, those in which the β-sheet structure is formed from one peptide chain are used as peptide structure units in the third embodiment. That is, each peptide chain which forms β-sheet structure is folded at the terminal of β-strand, and principal chain of the peptide structure is not severed at the folding part 4 and amino acid residues are connected by peptide bond. In the center of FIG. 4, there is a first peptide structure unit, namely a β-sheet structure 12 in which a functional material F is connected to the amino terminal via a connecting group and a three times folded structure (three β-strands in a row) is formed. Standing in a row with this, second peptide structure units 11 and 13 of a four times folded (four β-strands in a row) β-sheet structure in which amino group or carboxyl group is connected to the terminal are positioned.

In this embodiment, a row of these peptide structure units constitutes a functional peptide fiber 10. In this connection, a functional material 2 is schematically shown repeatedly in the drawing, but since their average intervals change in response to the mixing ratio of the first and second peptide structure units, the functional materials are not always arranged periodically over the entire structure. In this connection, when three-dimensionally large structure units and small structure units are mixed in the peptide chain folding parts and the functional material, there will be a case in which a space can be kept between the functional materials by restricting the large peptide structure units to adjoin each other making use of their steric hindrance.

In this case, each peptide structure unit is connected by one peptide chain but severed from adjoining peptide structure units, namely, principal chains of peptide chains are not connected by peptide bond. By effecting such a constitution, it becomes possible to arrange a large number of connecting parts in the functional peptide fiber, which can connect a large number of functional materials, and to recover peptide chains easily from the functional peptide fiber after its use.

In this connection, as described in the foregoing, the number of amino acid residues constituting a β-strand, namely one of the arrow moieties in the drawing, is preferably from 5 to 30, and the number of amino acid residues of the whole peptide chains constituting each peptide structure unit is preferably 200 or less. In case that the number of residues exceeds 200, folding of the peptide chain cannot be effected suitably so that it sometimes becomes difficult to constitute a peptide fiber stably. Accordingly, it is desirable to control the folding number of peptide chain (or the number of peptide β-strands) to 40 or less in a peptide structure unit.

Production Method of Functional Peptide Fiber

In order to achieve the object described in the foregoing, the method for producing the functional peptide fiber of the invention is characterized in that two or more peptide structure units which are two or more peptide structure units each containing at least one peptide chain, wherein a functional material or a connecting substance which connects to the functional material, or the functional material via the connecting substance, is connected to a peptide chain contained in at least one peptide structure unit of the two or more peptide structure units, are mixed in an aqueous solution to effect formation of a β-sheet structure between a peptide chain contained in the peptide structure unit and a peptide chain contained in other peptide structure unit, thereby structuring them into a fibrous form.

As described in the foregoing, the peptide structure unit contains one or more peptide chains which form a β-sheet structure together with peptide chains of other structure unit or the β-sheet structure itself, and it can be used by mixing with a peptide chain which is structured into a β-sheet form from an α-helix structure spontaneously in a solution. In that case, a peptide chain to which a functional material is connected in advance directly or via a connecting substance may be used, or the functional material may be bonded via a connecting substance after making a peptide fiber by constituting the peptide chain into such a state that the functional material is not connected thereto at first but a connecting substance is connected. By doing this, it becomes possible to incorporate a functional material into the functional peptide fiber, even in case that the material becomes a structure which can hardly take a β-sheet structure when connected to the peptide chain in advance.

Also, it is desirable that the connecting substance to be connected to the peptide chain is a material which connects to a functional material with a biochemical specificity or one of a pair of materials which connect with mutual biochemical specificity. This facilitates control of the connecting point of the functional material in the functional peptide fiber.

In this connection, examples of the term "material having specificity" as used herein include those which cause a covalent bond or hydrogen bond simply accompanied by a chemical reaction, a coordinate bond between a metal and its ligand and a bond having biochemical specificity. However, when materials which particularly generate a bond having biochemical specificity, such as avidin and biotin, an enzyme and its substrate or inhibitor or an antibody and its antigen, are used, they are desirable from the viewpoint that specification of the connecting point of the functional material becomes easy.

Fourth Embodiment

This embodiment relates to a method for the production of the functional peptide fiber of the invention.

That is, the β-peptide fiber to be used in this embodiment can be produced for example by the following method.

Firstly, the peptide having an α-helix structure or a random coil structure or already having a β-sheet structure, to be used as the material can be synthesized by a method such as 9-fluorenylmethoxycarbonyl (Fmoc) method or t-butoxycarbonyl (Boc) solid phase or liquid phase method, by reference to the report (Takahashi, Y., Ueno, A. and Mihara, H., *ChemBioChem*, 2, pp. 75-79 (2001). A hydrophobic group necessary for the β-form construction is introduced into the amino terminal of this peptide. Examples of the hydrophobic group to be used herein include an acyl group such as adamantane carbonyl group or octanoyl group, a hydrophobic amino acid such as leucine, isoleucine, valine or phenylalanine and a pigment such as a fluorescence group. Introduction of the hydrophobic group can be carried out, e.g., by a method similar to the case of usual amino acid introduction which uses a condensing agent such as carbodiimide. Also, similar effect can be obtained by increasing hydrophobicity of the peptide moiety without using a hydrophobic group. The thus obtained peptide may be purified as occasion demands by a method such as reverse phase HPLC and further verified as occasion demands by its molecular weight measurement and amino acid analysis by a means such as MALDI-TOFMS (laser ionization time of flight mass spectrometer).

The hydrophobic group-introduced peptide having an α-helix structure or a random coil structure or already having a β-sheet structure is rearranged into a β-peptide fiber structure spontaneously and self-catalytically under a uniform environment. The term "under a uniform environment" as used herein means a uniform environment in an aqueous solution which contains or does not contain a small amount of an organic solvent. Illustratively, it may be carried out in a buffer solution such as Tris-HCl buffer at a peptide concentration of approximately from 1 µM to 10 mM. Structure of the peptide can be examined using circular dichroism (CD) spectrum, and formation of β-peptide fiber can be examined using a transmission electron microscope (TEM), an atomic force microscope (AFM) or a peptide-specific connecting pigment (e.g., Thioflavine T or Congo Red).

Next, a functional material is bonded to the peptide chain terminal via a connecting substance. This connecting method may be optionally decided in response to the functional material and connecting substance. Its examples include a method which uses avidin and biotin wherein biotin group is covalently bonded to the peptide chain terminal and avidin is bonded non-covalently, a method which uses an enzyme and its substrate, inhibitor or coenzyme wherein the substrate, inhibitor or coenzyme is covalently bonded to the peptide and the enzyme is bonded non-covalently and a method which uses a metal and its ligand wherein the ligand is covalently bonded to the peptide and the metal is bonded coordinately.

Alternatively, a functional material or a connecting substance may be introduced instead of the hydrophobic group at a stage of monomer having no α-helix structure or specific three-dimensional structure. By doing this, the interval between functional materials can be controlled by changing ratio of the functional material and hydrophobic group. That is, it becomes possible to control density of the functional material when a monomer peptide such as of α-helix structure having no functional material and a peptide of α-helix structure, namely a peptide of α-helix structure having a hydrophobic group on its terminal further having a functional material (or a connecting substance), are mixed and then structured into a β-sheet form. Also, it is possible to effect the same control when a monomer peptide such as of α-helix structure having a hydrophobic group on its terminal, constructed into β-form in advance, and a peptide such as of α-helix structure having a functional material (or a connecting substance) are mixed and then structured into a β-sheet form.

Also, in case that a connecting substance is introduced into a peptide, the functional fiber of the invention can be obtained by further connecting it with a functional material or a connecting substance to which the functional material is bonded. In this connection, a connecting substance to which a functional material is added instead of a hydrophobic group may be introduced at a stage of a monomer peptide such as of α-helix structure.

The method of the invention for recovering peptide chains is characterized in that the functional peptide fiber of the invention is cut into two or more peptide chains by mixing it in an organic solvent or an acid or alkali solution, and then the two or more peptide chains are recovered from the organic solvent. According to this method, the peptide chains can be recovered with a high yield and easily recycled so that it becomes possible to use the functional peptide fiber broadly as a reusable material gentle to the environment.

Different from natural peptide fibers, in the functional peptide fiber of the invention, peptide chains contained in β-sheet structure-forming different peptide structure units do not form peptide bond, so that carboxyl terminal and amino terminal of peptide chains to which functional materials can be connected are increased in response to the number of β-sheet-constituting peptide chains. What is more, since the β-sheet structure is a structure in which peptide β-strands are arranged in a row with a minimum width of about 10 nm, the peptide terminals are also arranged in a row periodically and with minute intervals, so that when functional materials are connected to the peptide chain terminals in two or more peptide structure units, an array structure can be formed and it becomes possible to vary intervals of functional materials and to effect their periodical configuration and orientation.

Accordingly, making use of its characteristics, it becomes possible to use the functional peptide fiber of the invention in broad applications including medical engineering materials such as of cell engineering and tissue engineering, nano-technology materials such as micro-array for molecule detection, optical materials and molecular and electronic materials.

EXAMPLES

The present invention will be illustrated in greater detail with reference to the following Examples, but the invention should not be construed as being limited thereto.

Example 1

(1) Synthesis of Peptides Having α-helix Structure

Peptides having the structure set forth in SEQ ID NO: 1 were designed and synthesized into amphipathic 2α-helix structure having the structure set forth in SEQ ID NO: 2.

An adamantine carbonyl group was introduced into the amino terminal as a hydrophobic group to obtain a peptide (designated "Ad-2α" (SEQ ID NO: 2)). In the same manner, a peptide (designated "Bx-2α" (SEQ ID NO: 2)) having a biotinylated amino terminal was designed and synthesized. These parallel double chain peptides were synthesized by the formation of intermolecular disulfide bonds between cysteine residues (amino acid residue 17 of SEQ ID NO: 2) connected to carboxyl terminals of β-Ala (amino acid residue 16 of SEQ ID NO: 2) of two single chains of a peptide designated "Ad-1α" (SEQ ID NO: 1) or two single chains of a peptide designated "Bx-1α" (SEQ ID NO: 1). The single chain peptides were also synthesized, as described below.

Synthesis of the single chain peptides was carried out by the general 9-fluorenylmethoxycarbonyl (Fmoc) solid phase method described, e.g., by Takahashi, Y., Ueno, A. and Mihara, H., in Chem., Eur. J., 4, pp. 2475-2484. That is, Ad-1α (SEQ ID NO: 1) and Bx-1α (SEQ ID NO: 1) were synthesized by elongating Fmoc amino acid derivatives (each in 3 to 6 equivalent) corresponding to their amino acid sequences on Rink amide solid phase method resin (200 mg, 0.10 mmol) using a condensing agent, e.g., 2-(1H-benzotria-zol-1-yl)-1,1,3,3-tetramethyluronium hexafluorophosphate (HBTU) (yield, about 50%).

The double chain peptides were synthesized by adding 1 M HCl (5 ml) to dimethyl sulfoxide (5 ml) solution of the single chain peptides (100 mg) and stirring the mixture at room temperature for 1 day to form the disulfide bonds. The thus obtained double chain peptides were purified by a reverse phase HPLC (LC-10, mfd. by Shimadzu), subjected to molecular weight measurement by MALDI-TOFMS (laser ionization time of flight mass spectrometer) (MALDI III type, mfd. by Shimadzu) and identified by amino acid analysis (phenylthiocarbamoylamino acid method, using LC-10 type HPLC mfd. by Shimadzu).

(2) Rearrangement from α-helix Structure to α-sheet Structure

An aqueous solution (20 mM, Tris-HCl buffer, pH 7.4) of the amino terminal-biotinylated peptide (Bx-2α) was prepared and its behavior was observed. By examining structure of the peptide using circular dichroism (CD) spectrum (measured at room temperature in Tris-HCl buffer having a peptide concentration of 10 μM, by J-720 circular dichroism dispersion meter mfd. by Japan Spectroscopic), its rearrangement from α-helix structure to β-sheet structure was confirmed. Also, formation of β-peptide fiber was confirmed using a transmission electron microscope (TEM) (Type H-7500 mfd. by Hitachi, negative staining with tungsten phosphate), an atomic force microscope (AFM) (Nanoscope IIIa, mfd. by Japan Beaco) and a peptide-specific connecting pigment (Thioflavine T) (6 μM of Thioflavine T is added to a Tris-HCl buffer containing 12 μM of the peptide and immediately excited at 435 nm, and formation of β-fiber is detected based on the increase in the fluorescence intensity at 482 nm) and a pigment (Congo Red) (9 μM of Congo Red is added to a Tris-HCl buffer containing 12 μM of the peptide and stirred for 30 minutes, and then visible light absorption spectrum is measured and formation of β-fiber is detected based on the increase in the absorption strength at 540 nm).

(3) Addition of Avidin Protein

Streptavidin (10 μl, from 1 to 100 μM in concentration) was allowed to react with the peptide connecting fiber (100 μl, from 1 to 1,000 μM in concentration).

As the result, it was able to obtain a functional peptide fiber to which the functional material was bonded. Since streptavidin is a protein which can form various complexes with other functional materials such as other proteins, enzymes, fluorescence groups and metals, it can be used in materials in which functional materials are sequenced making use of this property.

In this connection, avidin is not limited to streptavidin and other sources such as egg avidin can also be used, but it is desirable to use streptoavidin in view of its easy handling.

Example 2

A functional fiber in which intervals between functional materials were controlled was obtained by carrying out the same procedure of Example 1, except that both of the peptide (Ad-2α) in which adamantane carbonyl group was introduced into the amino terminal as a hydrophobic group and the peptide (Bx-2α) whose amino terminal was biotinylated, obtained in Example 1(1), were used in 1(2) (from 1 to 1,000 μM in concentration, from 1:1 to 100:1 in molar ratio).

Example 3

When a peptide in which its amino terminal was biotinylated and further connected with avidin protein was produced instead of the peptide (Bx-2α) whose amino terminal was biotinylated in Example 1(1), and it was used in 1(2), it was able to form it into a β-peptide fiber.

Example 4

Addition of Functional Materials by Biotin-avidin Connecting Group

Formation of β-peptide fibers was effected in the same manner as in Examples 1 to 3 using streptavidin to which a fluorescence dye, texas red or fluorescein, was bonded; streptavidin to which a photochromic dye, spiropyran or azobenzene, was bonded; streptavidin to which gold line particles were bonded; and streptoavidin to which a protein (enzyme), horseradish peroxidase, alkaline phosphatase, protein G or immunoglobulin G antibody, was bonded, instead of the streptavidin in the streptavidin protein connecting type β-peptide fibers prepared in Examples 1 to 3.

Example 5

Addition of Functional Material by Enzyme-coenzyme Connecting Group

Instead of the biotin group-bonded peptide prepared in Example 1, a peptide in which a coenzyme (iron heme) was connected to the amino terminal by covalent bond was synthesized in the same manner. After making the iron heme peptide into a β-fiber form, a β-fiber to which apocytochrome c was bonded as a functional material (protein) via the iron heme on the fiber was prepared.

Example 6

Addition of Functional Material by Metal-ligand Connecting Group

Instead of the biotin group-bonded peptide prepared in Example 1, a peptide in which an iminodiacetic acid derivative was connected to the amino terminal by covalent bond was synthesized in the same manner. After making the iminodiacetic acid peptide into a β-fiber form, a β-fiber to which iron, copper, chromium, cobalt or calcium ion was bonded as a functional material via the iminodiacetic acid group on the fiber was prepared.

Example 7

Preparation of Enzyme-linked Immunosorbent Assay (ELISA) Test Material

Using an anti-rabbit goat antibody-bonded β-fiber material obtained by the method shown in Example 4, an enzyme-linked immunosorbentassay (ELISA) test was carried out for quickly determining rabbit antibody titer in a solution by allowing the rabbit antibody to react with horseradish peroxidase-linked goat antibody.

The goat antibody-bonded β-fiber (1 μM) was processed into a sheet having a film thickness of about 100 to 1,000 μm. A solution (1 μl) prepared by changing concentration of the rabbit antibody in order within the range of from 0.1 to 100 nM was spotted on the sheet to a diameter of about 2 mm to effect connecting of the antibody. After washing, this, was allowed to react with the horseradish peroxidase-linked anti-rabbit goat antibody (100 μM), washed and then allowed to react with 3,3',5,5'-tetramethylbenzidine as the substrate, and the amount of rabbit antibody was calculated by colorimetric determination of the enzyme-dependent colored amount. It was able to develop an enzyme-linked immunosorbent assay (ELISA) test material as a reusable peptide sheet, without using a plastic plate which is discharged into the environment like the case of the conventional method.

Example 8

Recovery and Reusability Test of Functional β-peptide Fiber

This β-peptide fiber is a self-organizing aggregate material comprised of non-covalent bonds. Accordingly, it is possible to recycle the β-peptide fiber by cutting it into one molecular un-aggregated state by the use of an organic solvent. A mixed fiber (10 μM) of Bx-2α and Ad-2α was dissolved in methanol, and the peptides were immediately obtained as precipitate using ether (recovery yield 92%). It was able to obtain the same physical properties by dissolving the recovered peptides in water as such and thereby making them into the β-fiber again.

Thus, as has been described in the foregoing, according to the functional peptide fiber of the invention, desired functions can be added to the peptide fiber and the fiber can be recovered and recycled because of the use of β-sheet structure as the base.

While the invention has been described in detail and with reference to specific examples thereof, it will be apparent to one skilled in the art that various changes and modifications can be made therein without departing from the spirit and scope thereof.

The present invention is based on Japanese Patent Application No. 2002-49977, the contents thereof being herein incorporated by reference.

What is claimed is:

1. A method for preparing a functional peptide fiber bonded to a functional material via a pair of connecting substances, comprising:
providing a plurality of peptide structure units having an α-helix or a β-sheet structure, each peptide structure unit comprising a peptide chain, wherein the α-helix structure has a hydrophobic group at an N-terminal or C-terminal of the peptide chain;
connecting a first connecting substance to the peptide chain;
forming a β-sheet of fibrous form by mixing the peptide structure units in an aqueous solution; and
bonding a second connecting substance to the first connecting substance, the second connecting substance being connected to a functional material and having a biochemical specificity for the first connecting substance;
wherein:
the first connecting substance is one of a biotin group and an avidin group, one of an antibody and an antigen, one of an enzyme and a substrate, an inhibitor or a coenzyme, or one of a metal and a ligand of the metal;
the second connecting substance is the other of the biotin group and the avidin group, the other of the antibody and the antigen, the other of the enzyme and the substrate, the inhibitor or the coenzyme, or the other of the metal and the ligand of the metal; and
the functional material is selected from the group consisting of proteins, carbohydrates, lipids, coenzyme, pigments comprising fluorescence groups, liquid crystalline molecules and metallic ligands.

2. The method according to claim 1, wherein the first connecting substance is connected to an amino terminal or a carboxyl terminal of the peptide chain.

3. The method according to claim 1, wherein a hydrophobic group is connected to an amino terminal or carboxyl terminal of the peptide chain in the α-helix structure.

4. The method according to claim 1, wherein the plurality of peptide structure units have an α-helix structure before forming the β-sheet.

5. The method according to claim 1, wherein the peptide structure unit comprises a pair of peptide chains in which adjacent terminals thereof are bonded to each other.

6. The method according to claim 5, wherein the terminals of the peptide chains are disulfide-bonded.

7. The method according to claim 1, wherein each β-strand of the β-sheet comprises from 5 to 30 amino acid residues.

8. The method according to claim 1, wherein the peptide chain comprises 200 or less amino acid residues.

9. A method for recovering peptide chains, comprising:
mixing the functional peptide fiber prepared by the method according to claim 1 in an organic solvent, an acidic solution, or an alkaline solution to divide the functional peptide fiber into a plurality of peptide chains; and
recovering the plurality of peptide chains from the organic solvent, the acidic solution, or the alkaline solution.

10. The method according to claim 1, wherein:
the first connecting substance is one of a biotin group and an avidin group, or one of an antibody and an antigen;
the second connecting substance is the other of the biotin group and the avidin group, or the other of the antibody and the antigen; and
the functional material is texas red, flourescein, spiropyran, azobenzene, gold fine particles, horseradish peroxidase, alkaline phosphatase, protein G, or immunoglobulin G antibody.

11. The method according to claim 10, wherein:
the first connecting substance is the biotin group; and
the second connecting substance is streptavidin.

12. The method according to claim 1, wherein:
the first connecting substance is one of iron heme and apocytochrome C;
the second connecting substance is the other of iron heme and apocytochrome C; and
the functional material is texas red, flourescein, spiropyran, azobenzene, gold fine particles, horseradish peroxidase, alkaline phosphatase, protein G, or immunoglobulin G antibody.

13. The method according to claim 1, wherein:
the first connecting substance is an iminodiacetic acid compound;
the second connecting substance is iron, copper, chromium, cobalt or calcium ion; and
the functional material is texas red, flourescein, spiropyran, azobenzene, gold fine particles, horseradish peroxidase, alkaline phosphatase, protein G, or immunoglobulin G antibody.

* * * * *

```
                        SEQUENCE LISTING

<160> NUMBER OF SEQ ID NOS: 2

<210> SEQ ID NO 1
<211> LENGTH: 17
<212> TYPE: PRT
<213> ORGANISM: Artificial Sequence
<220> FEATURE:
<223> OTHER INFORMATION: synthesized peptide having a-helix structure
<220> FEATURE:
<221> NAME/KEY: MISC_FEATURE
<222> LOCATION: (1)..(1)
<223> OTHER INFORMATION: modified by biotin or by adamantane carbonyl
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (16)..(16)
<223> OTHER INFORMATION: beta-Ala
<220> FEATURE:
<221> NAME/KEY: MISC_FEATURE
<222> LOCATION: (17)..(17)
<223> OTHER INFORMATION: modified by acetamidomethyl
<220> FEATURE:
<221> NAME/KEY: MOD_RES
<222> LOCATION: (17)..(17)
<223> OTHER INFORMATION: AMIDATION

<400> SEQUENCE: 1

Ala Ala Leu Glu Gln Lys Leu Ala Ala Leu Glu Gln Lys Leu Ala Ala
1               5                   10                  15

Cys

<210> SEQ ID NO 2
<211> LENGTH: 34
<212> TYPE: PRT
<213> ORGANISM: Artificial Sequence
<220> FEATURE:
<223> OTHER INFORMATION: synthesized peptide having a-helix structure
<220> FEATURE:
<221> NAME/KEY: MISC_FEATURE
<222> LOCATION: (1)..(1)
<223> OTHER INFORMATION: modified by biotin or by adamantane carbonyl
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (16)..(16)
<223> OTHER INFORMATION: beta-Ala
<220> FEATURE:
<221> NAME/KEY: MOD_RES
<222> LOCATION: (17)..(17)
<223> OTHER INFORMATION: AMIDATION
<220> FEATURE:
<221> NAME/KEY: DISULFID
<222> LOCATION: (17)..(17)

<400> SEQUENCE: 2
```

```
-continued

Ala Ala Leu Glu Gln Lys Leu Ala Ala Leu Glu Gln Lys Leu Ala Ala
1               5                   10                  15

Cys Cys Ala Ala Leu Lys Gln Glu Leu Ala Ala Leu Lys Gln Glu Leu
            20                  25                  30

Ala Ala
```